US00PP33275P3

(12) United States Plant Patent
van Sambeek

(10) Patent No.: US PP33,275 P3
(45) Date of Patent: Jul. 20, 2021

(54) ***PHLOX* PLANT NAMED 'DOPHLOXEARPUPINEYE'**

(50) Latin Name: *Phlox paniculata*
Varietal Denomination: Dophloxearpupineye

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 241 days.

(21) Appl. No.: 16/350,647

(22) Filed: Dec. 14, 2018

(65) Prior Publication Data

US 2020/0196506 P1 Jun. 18, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

(56) References Cited

PUBLICATIONS

Dummen Orange Catalog—Unrooted Perennials, 2017-2018, 7 pages total.*

* cited by examiner

*Primary Examiner* — Susan McCormick Ewoldt
(74) *Attorney, Agent, or Firm* — C. A. Whealy

(57) ABSTRACT

A new and distinct cultivar of *Phlox* plant named 'Dophloxearpupineye', characterized by its upright, outwardly spreading and mounding plant habit; vigorous growth habit; early and freely flowering habit; light purple violet-colored flowers with red purple-colored centers; and good garden performance.

1 Drawing Sheet

Botanical designation: *Phlox paniculata.*
Cultivar denomination: 'DOPHLOXEARPUPINEYE'.

BACKGROUND OF THE INVENTION

The present invention relates to a new and distinct cultivar of *Phlox* plant, botanically known as *Phlox paniculata* and hereinafter referred to by the name 'Dophloxearpupineye'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from a self-pollination made by the Inventor in July, 2013 in Aalsmeer, The Netherlands, of a proprietary selection of *Phlox paniculata* identified as code number PA07-000015-010, not patented. The new *Phlox* plant was discovered and selected by the Inventor as a single flowering plant from within the progeny of the stated self-pollination in a controlled environment in Aalsmeer, The Netherlands in July, 2014.

Asexual reproduction of the new *Phlox* plant by cuttings in a controlled environment in Aalsmeer, The Netherlands since July, 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophloxearpupineye' These characteristics in combination distinguish 'Dophloxearpupineye' as a new and distinct *Phlox* plant:

1. Upright, outwardly spreading and mounding plant habit.
2. Vigorous growth habit.
3. Early and freely flowering habit.
4. Light purple violet-colored flowers with red purple-colored centers.
5. Good garden performance.

Plants of the new *Phlox* differ primarily from plants of the parent selection in flower color as plants of the new *Phlox* have light purple violet-colored flowers with red purple-colored centers whereas plants of the parent selection have light purple violet-colored flowers without a contrasting-colored center.

Plants of the new *Phlox* can be compared to plants of *Phlox paniculata* 'Sweet Summer Snow', not patented. In side-by-side comparisons, plants of the new *Phlox* and 'Sweet Summer Snow' differ in the following characteristics:

1. Plants of the new *Phlox* are smaller than plants of 'Sweet Summer Snow'.
2. Plants of the new *Phlox* have smaller leaves than plants of 'Sweet Summer Snow'.
3. Plants of the new *Phlox* are more freely flowering than plants of 'Sweet Summer Snow'.

4. Plants of the new *Phlox* flower about two weeks earlier than plants of 'Sweet Summer Snow'.
5. Plants of the new *Phlox* have smaller flowers than plants of 'Sweet Summer Snow'.
6. Plants of the new *Phlox* and 'Sweet Summer Snow' differ in flower color as plants of the new *Phlox* have light purple violet-colored flowers with red purple-colored centers whereas plants of 'Sweet Summer Snow' have white-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Dophloxearpupineye' grown in a container.

DETAILED BOTANICAL DESCRIPTION

The aforementioned photograph and following observations, measurements and values describe plants grown during the summer in 13-cm containers in an outdoor nursery in Aalsmeer, The Netherlands and under cultural practices typical of commercial *Phlox* production. During the production of the plants, day temperatures averaged 21° C. and night temperatures averaged 15° C. Plants were pinched one time about one week after planting rooted young plants and were three months old when the photograph was taken and 20 weeks old when the description was taken. In the following description, color references are made to The Royal Horticultural Society Colour Chart, 2001 Edition, except where general terms of ordinary dictionary significance are used.

Botanical classification: *Phlox paniculata* 'Dophloxearpupineye'.

Parentage:

*Female, or seed, parent*.—Proprietary selection of *Phlox paniculata* identified as code number PA07-000015-010, not patented.

*Male, or pollen, parent*.—Proprietary selection of *Phlox paniculata* identified as code number PA07-000015-010, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright, outwardly spreading and mounding plant habit; vigorous growth habit; moderate growth rate.

*Plant height*.—About 25 cm to 30 cm.

*Plant width* (*spread*).—About 30 cm.

*Lateral branches*.—Branching habit: Freely branching, about six primary lateral branches develop after pinching. Length: About 25 cm. Internode length: About 2 cm to 4 cm. Strength: Strong. Aspect: Upright to outwardly spreading. Texture: Smooth, glabrous. Color: Close to 144A tinged with close to 165A.

Leaf description:

*Arrangement*.—Opposite, simple.

*Length*.—About 5 cm to 6 cm.

*Width*.—About 2 cm.

*Shape*.—Ovate to elliptical.

*Apex*.—Acuminate.

*Base*.—Attenuate.

*Margin*.—Entire.

*Texture, upper and lower surfaces*.—Smooth, glabrous.

*Venation pattern*.—Pinnate, reticulate.

*Color*.—Developing and fully expanded leaves, upper surface: Close to 139A; venation, close to 146D. Developing and fully expanded leaves, lower surface: Close to 189A; venation, close to 139D.

*Petioles*.—Length: About 2 mm. Diameter: About 2 mm. Strength: Strong, flexible. Texture, upper and lower surfaces: Smooth, glabrous. Color, upper and lower surfaces: Close to 144D tinged with close to 79A.

Flower description:

*Flower type and flowering habit*.—Single rotate and salverform flowers arranged in compound terminal and lateral panicles; flowers face mostly upright to outwardly; freely flowering habit with about 50 to 60 flowers per inflorescence and about 1,000 flowers developing per plant during the flowering season.

*Fragrance*.—Slightly fragrant, pleasant.

*Natural flowering season*.—Early flowering habit, plants begin flowering about ten weeks after planting; plants flower in July in The Netherlands; flowers not persistent.

*Flower buds*.—Height: About 1.3 cm. Diameter: About 3 mm. Shape: Conical. Color: Close to 2D becoming closer to 83B with development.

*Inflorescence height*.—About 12 cm.

*Inflorescence diameter*.—About 13 cm.

*Flower diameter*.—About 2.5 cm.

*Flower depth*.—About 2.2 cm.

*Flower throat diameter*.—About 2.5 mm.

*Flower tube length*.—About 1.8 cm.

*Flower diameter, proximally*.—About 2 mm.

*Petals*.—Quantity per flower: Typically five in a single whorl; petals fused at the base into a narrow tube. Lobe length: About 1.1 cm. Lobe width: About 9 mm. Lobe shape: Roughly orbicular. Lobe apex: Rounded. Lobe margin: Entire. Lobe texture, upper and lower surfaces: Smooth, glabrous. Throat texture: Pubescent; slightly rough. Tube texture: Pubescent. Color: When opening and fully opened, upper surface: Close to 155C tinged with close to 81B; towards the throat, close to 59A; venation, similar to lamina colors; with development color becoming closer to 155C slightly tinged with close to 81B. When opening and fully opened, lower surface: Close to 82A; venation, close to 82A; with development, color becoming closer to 155C tinged with close to 82A. Throat: Close to 71A; venation, close to 71A. Tube: Close to 71A; venation, close to 71A.

*Sepals*.—Quantity per flower: Typically five in a single whorl, fused towards the base; calyx, campanulate. Length: About 9 mm. Width: About 1 mm. Shape: Narrowly deltoid. Apex: Acuminate. Margin: Entire. Texture, upper surface: Smooth, glabrous. Texture, lower surface: Pubescent. Color: When opening and fully opened, upper surface: Close to 146C. When opening and fully opened, lower surface: Close to 146C tinged with close to 187A.

*Peduncles*.—Length: About 7 cm to 8 cm. Diameter: About 1.5 mm. Strength: Moderately strong. Aspect: About 45° from lateral branch axis. Texture: Pubescent. Color: Close to 144A tinged with close to 165A.

*Pedicels*.—Length: About 7 mm. Diameter: About 1 mm. Strength: Moderately strong. Aspect: About 35° from peduncle axis. Texture: Pubescent. Color: Close to 144A.

*Reproductive organs*.—Stamens: Quantity per flower: Typically five. Filament length: About 2 mm. Filament color: Close to 155C. Anther length: About 2 mm. Anther color: Close to 8C. Pollen amount: Abundant. Pollen color: Close to 8D. Pistils: Quantity per flower: One. Pistil length: About 2 cm. Stigma shape: Cleft, three-parted. Stigma color: Close to 8C. Style length: About 1.7 cm. Style color: Close to 1D with a purplish blush. Ovary color: Close to 143A.

*Seeds and fruits*.—To date, seed and fruit development have not been observed on plants of the new *Phlox*.

Garden performance: Plants of the new *Phlox* have been observed to have good garden performance and to tolerate rain, wind and temperatures ranging from −20° C. to 35° C.

Pathogen & pest resistance: Plants of the new *Phlox* have not been observed to be resistant to pathogens and pests common to *Phlox* plants.

It is claimed:

1. A new and distinct *Phlox* plant named 'Dophloxearpupineye' as illustrated and described.

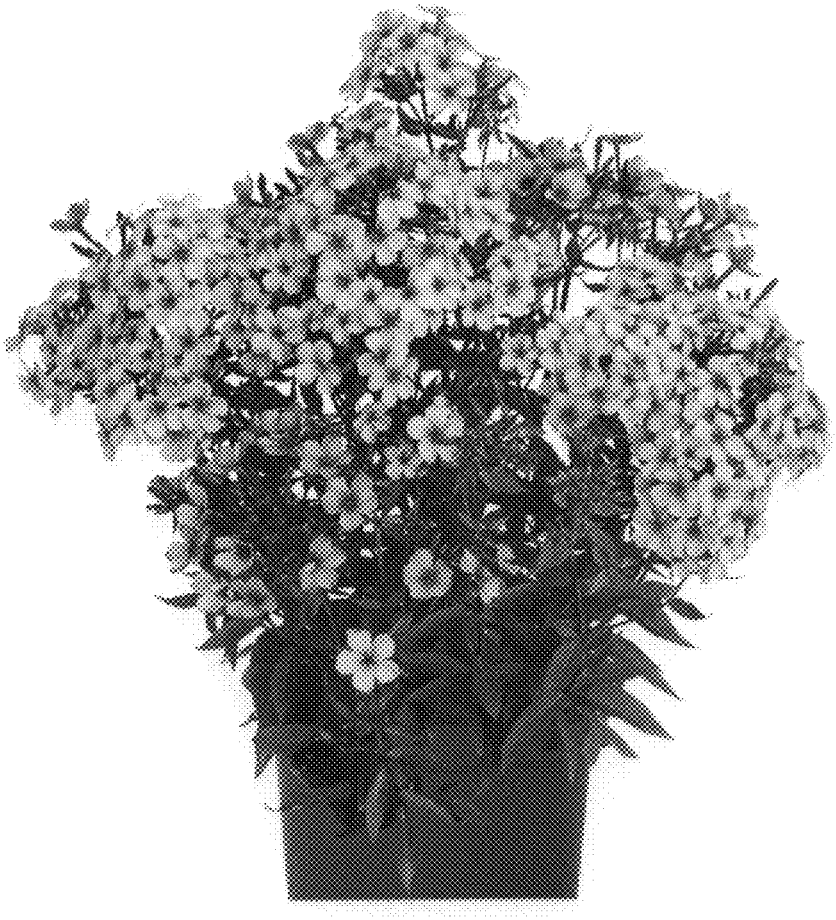

* * * * *